United States Patent [19]
Gers-Barlag et al.

[11] Patent Number: 5,961,959
[45] Date of Patent: Oct. 5, 1999

[54] COSMETIC AND DERMATOLOGICAL LIGHT PROTECTION FORMULATIONS HAVING A CONTENT OF TRIAZINE DERIVATIVES AND MONOESTERS AND DIESTERS OF BRANCHED ALKANECARBOXYLIC ACIDS AND DIGLYCEROL OR TRIGLYCEROL

[75] Inventors: Heinrich Gers-Barlag, Kummerfeld; Rainer Kröpke, Hamburg, both of Germany

[73] Assignee: Beiersdorf AG, Hamburg, Germany

[21] Appl. No.: 08/840,246

[22] Filed: Apr. 17, 1997

[30] Foreign Application Priority Data

Apr. 27, 1996 [DE] Germany ............... 196 16 926

[51] Int. Cl.⁶ .................. A61K 7/42; A61K 7/44
[52] U.S. Cl. .............. 424/59; 424/60; 424/401; 514/785
[58] Field of Search ............. 424/401, 59, 60, 424/70.9

[56] References Cited

U.S. PATENT DOCUMENTS

| | | | |
|---|---|---|---|
| 5,047,232 | 9/1991 | Kaplan | 424/59 |
| 5,147,644 | 9/1992 | Oppenlaender et al. | 424/401 |
| 5,302,376 | 4/1994 | Forestier et al. | 424/59 |
| 5,427,771 | 6/1995 | Grollier et al. | 424/59 |
| 5,489,431 | 2/1996 | Ascione et al. | 424/401 |
| 5,585,091 | 12/1996 | Pelzer et al. | 424/60 |

FOREIGN PATENT DOCUMENTS

| | | |
|---|---|---|
| 451461 | 10/1991 | European Pat. Off. . |
| 457687 | 11/1991 | European Pat. Off. . |
| 685223 | 12/1995 | European Pat. Off. . |
| 689828 | 1/1996 | European Pat. Off. . |
| 786246 | 7/1997 | European Pat. Off. . |
| 3206398 | 9/1983 | Germany . |
| 4409689 | 9/1995 | Germany . |
| WO 94/07460 | 4/1994 | WIPO . |
| WO 97/26857 | 7/1997 | WIPO . |

OTHER PUBLICATIONS

Sperling K: Kosmetik Rohstoffe, Wirkstoffe, Formulierungen Sofw–Journal Seifen, Oele, Fette, Wachse, pp. 661–662, XP000081197, Nov. 1989.

*Primary Examiner*—Thurman K. Page
*Assistant Examiner*—James M. Spear
*Attorney, Agent, or Firm*—Sprung Kramer Schaeffer & Briscoe

[57] ABSTRACT

Active compound combinations having a light-protection action and comprising (a) tris(2-ethylhexyl) 4,4',4"-(1,3,5-triazine-2,4,6-triyltriimino)-tris-benzoate and (b) one or more substances chosen from the group consisting of monoesters and diesters of branched alkanecarboxylic acids having a chain length of 10–24 carbon atoms and diglycerol or triglycerol.

22 Claims, No Drawings

COSMETIC AND DERMATOLOGICAL LIGHT PROTECTION FORMULATIONS HAVING A CONTENT OF TRIAZINE DERIVATIVES AND MONOESTERS AND DIESTERS OF BRANCHED ALKANECARBOXYLIC ACIDS AND DIGLYCEROL OR TRIGLYCEROL

DESCRIPTION

The present invention relates to cosmetic and dermatological light protection formulations, in particular skin-care cosmetic and dermatological light protection formulations.

The damaging effect of the ultraviolet part of solar radiation on the skin is generally known. While rays having a wavelength of less than 290 nm (the so-called UVC range) are absorbed by the ozone layer in the earth's atmosphere, rays in the range between 290 nm and 320 nm, the so-called UVB range, cause erythema, simple sunburn or even burns of greater or lesser severity.

The narrower range around 308 nm is stated as the erythema activity maximum of sunlight.

Numerous compounds are known for protection against UVB radiation, these mainly being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the so-called UVA range, it is also important to have available filter substances, since the rays in this range can also cause damage. Thus, it has been proved that UVA radiation leads to damage to the elastic and collagenic fibres of connective tissue, which makes the skin age prematurely, and that it is to be regarded as a cause of numerous phototoxic and photoallergic reactions. The damaging effect of UVB radiation can be intensified by UVA radiation.

However, UV radiation can also lead to photo chemical reactions, the photochemical reaction products then intervening in skin metabolism.

Such photochemical reaction products are chiefly free-radical compounds, for example hydroxyl radicals. Undefined free-radical photoproducts which are formed in the skin itself can also show uncontrolled secondary reactions because of their high reactivity. However, even singlet oxygen, a non-free-radical excited state of the oxygen molecule, may occur under UV irradiation, as can short-lived epoxides and many others. Singlet oxygen, for example, is distinguished from the triplet oxygen normally present (free-radical ground state) by an increased reactivity. Nevertheless, excited, reactive (free-radical) triplet states of the oxygen molecule also exist.

UV radiation is furthermore counted among ionizing radiation. There is therefore the risk of ionic species also being formed during UV exposure, which then in turn are capable of intervening oxidatively in bio-chemical processes.

An advantageous UVB filter is tris(2-ethylhexyl) 4,4',4"-(1,3,5-triazine-2,4,6-triyltriimino)-tris-benzoate, synonym: 2,4,6-tris-[anilino-(p-carbo-2'-ethyl-1'-hexyloxy)]-1,3,5-triazine.

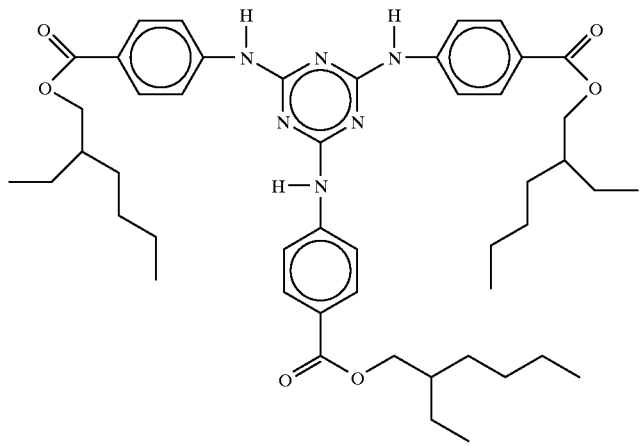

This UVB filter substance is marketed by BASF Aktiengesellschaft under the tradename UVINUL® T 150 and is distinguished by good UV absorption properties.

The main disadvantage of this UVB filter is its poor solubility in lipids. Known solvents for this UVB filter can dissolve not more than about 15% by weight of this filter, corresponding to about 1–1.5% by weight of dissolved, and therefore active, UV filter substance.

It was therefore surprising and unforeseeable to the expert that active compound combinations having a light-protection action of (a) tris(2-ethylhexyl) 4,4',4"-(1,3,5-triazine-2,4,6-triyltriimino)-tris-benzoate and (b) one or more substances chosen from the group consisting of monoesters and diesters of branched alkanecarboxylic acids having a chain length of 10–24 carbon atoms and diglycerol or triglycerol remedy the disadvantages of the prior art.

The invention also particularly relates to the use of one or more substances chosen from the group consisting of monoesters and diesters of branched alkane-carboxylic acids having a chain length of 10–24 carbon atoms and diglycerol or triglycerol as the solvent, solubilizing agent or solubilizer for tris(2-ethylhexyl) 4,4',4"-(1,3,5-triazine-2,4,6-triyltriimino)-tris-benzoate, in particular for use in light protection compositions.

The monoesters and diesters, used according to the invention, of branched alkanecarboxylic acids having a chain length of 10–24 carbon atoms and diglycerol or triglycerol are also given designations such as "diglycerol esters" and "triglycerol esters" below.

A prerequisite for possible use of the diglycerol esters and/or triglycerol esters used according to the invention for the purposes according to the invention is of course cosmetic and dermatological acceptability of the substances on which they are based.

According to the invention, it is possible to double the amounts of tris(2-ethylhexyl) 4,4',4''-(1,3,5-triazine-2,4,6-triyltriimino)-tris-benzoate employed in cosmetic or dermatological formulations compared with the prior art.

It was astonishing that addition of diglycerol esters and/or triglycerol esters used according to the invention causes stabilization of solutions of tris(2-ethylhexyl) 4,4',4''-(1,3,5-triazine-2,4,6-triyltriimino)-tris-benzoate, since the latter substance not only has a poor solubility but also readily crystallizes out of its solution again. The invention therefore also relates to a process for stabilizing solutions of tris(2-ethylhexyl) 4,4',4''-(1,3,5-triazine-2,4,6-triyltriimino)-tris-benzoate, characterized in that an active content of diglycerol esters and/or triglycerol esters used according to the invention is added to such solutions.

Combinations which comprise esters of isostearic acid as the diglycerol esters and/or triglycerol esters are particularly preferred, and triglycerol diisostearate, which, analogously to CTFA nomenclature, is also called polyglyceryl 3-diisostearate, is particularly preferred.

Such isostearic acid esters are obtainable, for example, under the product name "Lameform TGI" from the company Henkel KGaA.

The total amount of tris(2-ethylhexyl) 4,4',4''-(1,3,5-triazine-2,4,6-triyltriimino)-tris-benzoate in the finished cosmetic or dermatological formulations is advantageously chosen from the range of 0.1–10.0% by weight, preferably 0.5–6.0% by weight, based on the total weight of the formulations.

The total amount of one or more diglycerol esters and/or triglycerol esters used according to the invention in the finished cosmetic or dermatological formulations is advantageously chosen from the range of 0.1–25.0% by weight, preferably 0.5–15.0% by weight, based on the total weight of the formulations.

It is advantageous to choose weight ratios of tris(2-ethylhexyl) 4,4',4''-(1,3,5-triazine-2,4,6-triyl-triimino)-tris-benzoate and one or more diglycerol esters and/or triglycerol esters used according to the invention from the range from 1:10 to 10:1, preferably 1:4 to 4:1.

Cosmetic and dermatological formulations according to the invention advantageously furthermore comprise inorganic pigments based on metal oxides and/or other metal compounds which are sparingly soluble or insoluble in water, in particular the oxides of titanium ($TiO_2$), zinc (ZnO), iron (for example $Fe_2O_3$), zirconium ($ZrO_2$), silicon ($SiO_2$), manganese (for example MnO), aluminium ($Al_2O_3$) or cerium (for example $Ce_2O_3$), mixed oxides of the corresponding metals and mixtures of such oxides. The pigments are particularly preferably those based on $TiO_2$.

It is particularly advantageous in the context of the present invention, although not mandatory, if the inorganic pigments are present in hydrophobic form, i.e. they have been given a water-repellent treatment on the surface. This surface treatment can comprise providing the pigments with a thin hydrophobic coating by processes known per se.

One such process comprises, for example, producing the hydrophobic surface coating by a reaction according to

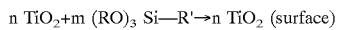

n and m in this equation are stoichiometric parameters which are to be inserted as desired and R and R' are the desired organic radicals. Pigments rendered hydrophobic as described analogously to DE-A 33 14 742, for example, are advantageous.

Advantageous $TiO_2$ pigments are obtainable, for example, under the tradenames MT 100 T from TAYCA, and furthermore M 160 from Kemira and T 805 from Degussa.

The cosmetic and/or dermatological light protection formulations according to the invention can have the customary composition and can be used for cosmetic and/or dermatological light protection, and furthermore for the treatment, care and cleansing of the skin and/or hair and as a make-up product in decorative cosmetics.

For use, the cosmetic and dermatological formulations according to the invention are applied to the skin and/or hair in an adequate amount in the manner customary for cosmetics.

Those cosmetic and dermatological formulations which are in the form of a sunscreen composition are particularly preferred. These advantageously additionally comprise at least one further UVA filter and/or at least one further UVB filter and/or at least one inorganic pigment, preferably an inorganic micropigment.

The cosmetic and dermatological formulations according to the invention can comprise cosmetic auxiliaries such as are usually used in such formulations, for example preservatives, bactericides, perfumes, substances for preventing foaming, dyestuffs, pigments which have a colouring action, thickeners, humidifying and/or humectant substances, fats, oils, waxes or other customary constituents of a cosmetic or dermatological formulation, such as alcohols, polyols, polymers, foam stabilizers, electrolytes, organic solvents or silicone derivatives.

An additional content of antioxidants is in general preferred. Favourable antioxidants which can be used in accordance with the invention are all the anti-oxidants which are suitable or customary for cosmetic and/or dermatological applications.

The antioxidants are advantageously chosen from the group consisting of amino acids (for example glycine, histidine, tyrosine and tryptophan) and derivatives thereof, imidazoles (for example urocaninic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, chlorogenic acid and derivatives thereof, liponic acid and derivatives thereof (for example di-hydroliponic acid), aurothioglucose, propylthiouracil and other thiols (for example thioredoxine, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homo-cysteine-sulphoximine, buthionine-sulphones and penta-, hexa- and heptathionine-sulphoximine) in very low tolerated dosages (for example pmol to μmol/kg), furthermore (metal) chelators (for example α-hydroxy-fatty acids, palmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, furfurylidene-sorbitol and derivatives thereof, ubiquinone and ubiquinol and derivatives thereof, vitamin C and derivatives (for example ascorbyl palmitate, Mg ascorbyl phosphate and ascorbyl acetate), tocopherols and derivatives (for example vitamin E acetate), vitamin A and derivatives (vitamin A palmitate) and coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

The amount of the abovementioned antioxidants (one or more compounds) in the formulations is preferably 0.001 to 30% by weight, particularly preferably 0.05–20% by weight, in particular 1–10% by weight, based on the total weight of the formulation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

The lipid phase can advantageously be chosen from the following group of substances:

mineral oils or mineral waxes;

oils, such as triglycerides of capric or of caprylic acid, but preferably castor oil;

fats, waxes and other naturally occurring and synthetic fat substances, preferably esters of fatty acids with alcohols of low C number, for example with isopropanol, propylene glycol or glycerol, or esters of fatty alcohols with alkanoic acids of low C number or with fatty acids;

alkyl benzoates;

silicone oils, such as dimethylpolysiloxanes, diethylpolysiloxanes, diphenylpolysiloxanes and mixed forms thereof.

The oily phase of the emulsions, oleogels or hydrodispersions or lipodispersions in the context of the present invention is advantageously chosen from the group consisting of esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, and from the group consisting of esters of aromatic carboxylic acids and saturated and/or unsaturated, branched and/or unbranched alcohols having a chain length of 3 to 30 C atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and naturally occurring mixtures of such esters, for example jojoba oil.

The oily phase can furthermore advantageously be chosen from the group consisting of branched and unbranched hydrocarbons and waxes, silicone oils and dialkyl ethers, from the group consisting of saturated or unsaturated, branched or unbranched alcohols, and from fatty acid triglycerides, in particular the triglycerol esters of saturated and/or unsaturated, branched and/or unbranched alkanecarboxylic acids having a chain length of 8 to 24, in particular 12–18 C atoms. The fatty acid triglycerides can advantageously be chosen, for example, from the group consisting of synthetic, semi-synthetic and naturally occurring oils, for example olive oil, sunflower oil, soya oil, groundnut oil, rapeseed oil, almond oil, palm oil, coconut oil, palm kernel oil and many of the like.

Any desired mixtures of such oil and wax components can also advantageously be employed in the context of the present invention. Where appropriate, it may also be advantageous to employ waxes, for example cetyl palmitate, as the sole lipid component of the oily phase.

The oily phase is advantageously chosen from the group consisting of 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicaprylyl ether.

Mixtures of $C_{12-15}$-alkyl benzoate and 2-ethylhexyl isostearate, mixtures of $C_{12-15}$-alkyl benzoate and isotridecyl isononanoate and mixtures of $C_{12-15}$-alkyl benzoate, 2-ethylhexyl isostearate and isotridecyl isononanoate are particularly advantageous.

Of the hydrocarbons, paraffin oil, squalane and squalene can advantageously be used in the context of the present invention.

The oily phase can furthermore advantageously have a content of cyclic or linear silicone oils or consist entirely of such oils, although it is preferable to use an additional content of other oily phase components in addition to the silicone oil or the silicone oils.

Cyclomethicone (octamethylcyclotetrasiloxane) is advantageously employed as a silicone oil to be used according to the invention. However, other silicone oils can also advantageously be be used in the context of the present invention, for example hexamethylcyclotrisiloxane, polydimethylsiloxane and poly(methylphenylsiloxane).

Mixtures of cyclomethicone and isotridecyl isononanoate and of cyclomethicone and 2-ethylhexyl isostearate are furthermore particularly advantageous.

If appropriate, the aqueous phase of the formulations according to the invention advantageously comprises alcohols, diols or polyols of low C number and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, and furthermore alcohols of low C number, for example ethanol, isopropanol, 1,2-propanediol and glycerol, and, in particular, one or more thickeners, which can advantageously be chosen from the group consisting of silicon dioxide, aluminium silicates, polysaccharides and derivatives thereof, for example hyaluronic acid, xanthan gum and hydroxypropylmethylcellulose, particularly advantageously from the group consisting of polyacrylates, preferably a polyacrylate from the group consisting of so-called Carbopols, for example Carbopols of types 980, 981, 1382, 2984 or 5984, in each case individually or in combination.

The cosmetic or dermatological light protection formulations advantageously comprise inorganic pigments, in particular micropigments, for example in amounts of 0.1% by weight to 30% by weight, preferably in amounts of 0.5% by weight to 10% by weight, but in particular 1% by weight to 6% by weight, based on the total weight of the formulations.

It is advantageous according to the invention to employ, in addition to the combinations according to the invention, oil-soluble UVA filters and/or UVB filters in the lipid phase and/or water-soluble UVA filters and/or UVB filters in the aqueous phase.

The light protection formulations according to the invention can advantageously comprise further substances which absorb UV radiation in the UVB range, the total amount of filter substances being, for example, 0.1% by weight to 30% by weight, preferably 0.5 to 10% by weight, in particular 1 to 6% by weight, based on the total weight of the formulations, in order to provide cosmetic formulations which protect the skin from the entire range of ultraviolet radiation. They can also serve as sunscreen agents.

The further UVB filters can be oil-soluble or water-soluble. Advantageous oil-soluble UVB filter substances are, for example:

3-benzylidenecamphor derivatives, preferably 3-(4-methylbenzylidene)camphor and 3-benzylidenecamphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

derivatives of benzophenone, preferably 2-hydroxy-4-methoxybenzophenone, 2-hydroxy-4-methoxy-4'-methylbenzophenone and 2,2'dihydroxy-4-methoxybenzophenone;

esters of benzalmalonic acid, preferably di(2-ethylhexyl) 4-methoxybenzalmalonate.

Advantageous water-soluble UVB filter substances are, for example:

salts of 2-phenylbenzimidazole-5-sulphonic acid, such as its sodium, potassium or its triethanol-ammonium salt and the sulphonic acid itself;

sulphonic acid derivatives of benzophenones, preferably 2-hydroxy-4-methoxybenzophenone-5-sulphonic acid and salts thereof;

sulphonic acid derivatives of 3-benzylidenecamphor, such as, for example, 4-(2-oxo-3-bornylidenemethyl)-benzenesulphonic acid, 2-methyl-5-(2-oxo-3-bornylidenemethyl)benzenesulphonic acid and salts thereof.

The list of further UVB filters mentioned which can be used in combination with the active compound combinations according to the invention is of course not intended to be limiting.

It may also be advantageous to combine the combinations according to the invention with further UVA filters which have usually been contained to date in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations and to formulations which comprise these combinations. The amounts used for the UVB combination can be employed.

It is furthermore advantageous to combine the active compound combinations according to the invention with further UVA and/or UVB filters.

It is also particularly advantageous to combine the active compound combinations according to the invention with salicylic acid derivatives, some representatives of which are known, which likewise can absorb UV radiation. Customary UV filters include

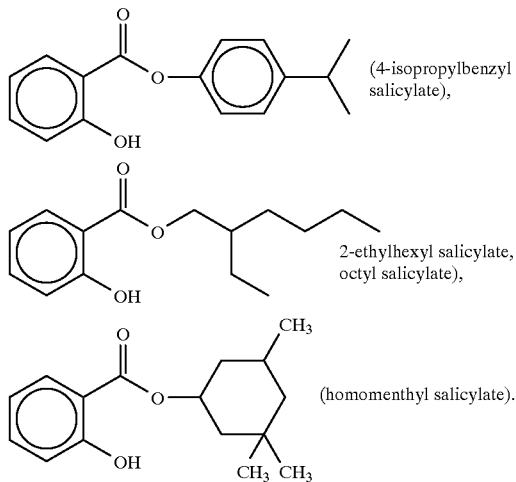

The invention also relates to a process for the preparation of the cosmetic and/or dermatological light protection formulations according to the invention, which is characterized in that tris(2-ethylhexyl) 4,4',4"-(1,3,5-triazine-2,4,6-triyltriimino)-tris-benzoate is suspended in a manner known per se in one or more diglycerol esters and/or triglycerol esters used according to the invention or an oily phase having a content of diglycerol esters and/or triglycerol esters used according to the invention, with uniform stirring and, if appropriate, while heating, and, if desired, the components are homogenized, the mixture is combined, if appropriate, with further lipid components and, if appropriate, with one or more emulsifiers, the oily phase is then mixed with the aqueous phase, into which a thickener has been incorporated, if appropriate, and which preferably has about the same temperature as the oily phase, if desired the components are homogenized, and the mixture is allowed to cool to room temperature. After cooling to room temperature, another homogenization can be carried out, especially if volatile constituents are still to be incorporated.

The following examples are intended to illustrate the present invention without limiting it. Unless stated otherwise, all the amounts, contents and percentages are based on the weight and the total amount or on the total weight of the formulations.

EXAMPLE 1

| O/W emulsion | % by weight |
|---|---|
| Stearic acid | 3.50 |
| Glycerol | 3.00 |
| Cetearyl alcohol | 0.50 |
| Preservative | q.s. |
| Perfume | q.s. |
| Caprylyl ether | 8.00 |
| Uvinul T150 | 5.00 |
| Lameform TGI | 12.0 |
| Sodium hydroxide (45% strength) | 0.33 |
| Carbomer | 0.20 |
| Water, demineralized | ad100.0 |

EXAMPLE 2

| W/O emulsion | % by weight |
|---|---|
| Arlacel 989 | 5.50 |
| Butylene glycol | 5.00 |
| Preservative | q.s. |
| Perfume | q.s. |
| Lameform TGI | 12.00 |
| Uvinul T150 | 5.00 |
| Cetearyl isononanoate | 6.00 |
| Carbomer | 0.20 |
| Water, demineralized | ad100.0 |

EXAMPLE 3

| Sunscreen balm | % by weight |
|---|---|
| Carbomer | 0.50 |
| Butylene glycol | 5.00 |
| Lameform TGI | 2.50 |
| Sodium hydroxide (45% strength) | 0.35 |
| Preservative | q.s. |
| Perfume | q.s. |
| Uvinul T150 | 5.00 |
| Hydroxypropylcellulose | 0.60 |
| Water, demineralized | ad100.0 |

We claim:

1. A cosmetic or dermatological formulation for protecting the skin of an individual from the effects of damaging UV light comprising a skin protective amount of an active compound combination of tris(2-ethylhexyl) 4,4',4"-(1,3,5-triazine-2,4,6-triyltriimino)-tris-benzoate and one or more substances chosen from the group consisting of monoesters and diesters of branched alkanecarboxylic acids having a chain length of 10–24 carbon atoms and diglycerol or triglycerol, wherein the total amount of said monoesters and diesters of branched alkane carboxylic acids having a chain length of 10–24 carbon atoms and diglycerol or triglycerol is sufficient to solubilize said tris(2-ethylhexyl)4,4',4"-(1,3,5-triazine-2,3,6-triyltriimino)-tris-benzoate.

2. A formulation according to claim 1, wherein the total amount of tris(2-ethylhexyl) 4,4',4"-(1,3,5-triazine-2,4,6-triyltriimino)-tris-benzoate in the formulation is chosen from the range of 0.1–10.0% by weight based on the total weight of the formulation.

3. A cosmetic or dermatological formulation for protecting the skin of an individual from the effects of damaging UV light comprising a skin protective amount of an active compound combination of tris(2-ethylhexyl) 4,4',4"-(1,3,5-triazine-2,4,6-triyltriimino)-tris-benzoate and one or more substances chosen from the group consisting of monoesters and diesters of branched alkanecarboxylic acids having a chain length of 10–24 carbon atoms and diglycerol or triglycerol, wherein the total amount of said one or more substances chosen from the group consisting of monoesters and diesters of branched alkane carboxylic acids having a chain length of 10–24 carbon atoms and diglycerol or triglycerol in the formulation is chosen from the range of 0.1–25.0% by weight based on the total weight of the formulation.

4. A formulation according to claim 3, wherein the total amount of said one or more substances chosen from the group consisting of monoesters and diesters of branched alkanecarboxylic acids having a chain length of 10–24 carbon atoms and diglycerol or triglycerol in the formulation is chosen from the range of 0.5–15.0% by weight based on the total weight of the formulation.

5. A method of protecting the skin of an individual from the effects of damaging UV light comprising applying to the skin of said individual a cosmetic or dermatological formulation according to claim 1.

6. A method according to claim 5, wherein the total amount of tris(2-ethylhexyl) 4,4',4"-(1,3,5-triazine-2,4,6-triyltriimino)-tris-benzoate in the formulation is chosen from the range 0.1–10.0% by weight based on the total weight of the formulation.

7. A method of protecting skin of an individual from the effects of damaging UV light comprising applying to said skin of said individual a cosmetic or dermatological formulation, wherein the total amount of said one or more substances chosen from the group consisting of monoesters and diesters of branched alkanecarboxylic acids having a chain length of 10–24 carbon atoms and diglycerol or triglycerol in the formulation is chosen from the range of 0.1–25.0% by weight based on the total weight of the formulation.

8. A method according to claim 7, wherein the total amount of said one or more substances chosen from the group consisting of monoesters and diesters of branched alkanecarboxylic acids having a chain length of 10–24 carbon atoms and diglycerol or triglycerol in the formulation is chosen from the range of 0.5–15.0% by weight based on the total weight of the formulation.

9. A cosmetic or dermatological formulation for protecting the skin of an individual from the effects of damaging UV light comprising a skin protective amount of an active compound combination of tris(2-ethylhexyl) 4,4',4"-(1,3,5-triazine-2,4,6-triyltriimino)-tris-benzoate, one or more substances chosen from the group consisting of monoesters and diesters of branched alkanecarboxylic acids having a chain length of 10–24 carbon atoms and diglycerol or triglycerol, and one or more salicylic acid derivatives selected from the group consisting of 4-isopropylbenzyl salicylate, 2-ethylhexyl salicylate, octyl salicylate and homomenthyl salicylate.

10. A formulation according to claim 9, wherein the weight ratios of tris(2-ethylhexyl) 4,4',4"-(1,3,5-triazine-2,4,6-triyltriimino)-tris-benzoate and one or more salicylic acid derivatives is chosen from the range from 1:10 to 10:1.

11. A formulation according to claim 10, wherein the weight ratios of tris (2-ethylhexyl) 4,4',4"-(1,3,5-triazine-2,4,6-triyltriimino)-tris-benzoate and one or more salicylic acid derivatives are chosen from the range 1:4 to 4:1.

12. A formulation according to claim 9, wherein the total amount of tris(2-ethylhexyl) 4,4',4"-(1,3,5-triazine-2,4,6-triyltriimino)-tris-benzoate in the formulation is chosen from the range of 0.1–10.0% by weight based on the total weight of the formulation.

13. A formulation according to claim 12, wherein the total amount of tris(2-ethylhexyl) 4,4',4"-(1,3,5-triazine-2,4,6-triyltriimino)-tris-benzoate in the formulation is chosen from the range 0.5–6.0% by weight based on the total weight of the formulation.

14. A formulation according to claim 9, wherein the total amount of one or more substances chosen from the group consisting of monoesters and diesters of branched alkanecarboxylic acids having a chain length of 10–24 carbon atoms and diglycerol or triglycerol in the formulation is chosen from the range of 0.1–25.0% by weight based on the total weight of the formulation.

15. A formulation according to claim 14, wherein the total amount of one or more substances chosen from the group consisting of monoesters and diesters of branched alkanecarboxylic acids having a chain length of 10–24 carbon atoms and diglycerol or triglycerol in the formulation is chosen from the range of 0.5–15.0% by weight based on the total weight of the formulation.

16. A method of protecting the skin of an individual from the effects of damaging UV light comprising applying to the skin of said individual a cosmetic or dermatological formulation comprising a skin protective amount of an active compound combination of tris(2-ethylhexy) 4,4',4"-(1,3,5-triazine-2,4,6-triyltriimino)-tris-benzoate, one or more substances chosen from the group consisting of monoesters and diesters of branched alkanecarboxylic acids having a chain length of 10–24 carbon atoms and diglycerol or triglycerol, and one or more salicylic acid derivatives chosen from the group consisting of 4-isopropylbenzyl salicylate, 2-ethylhexyl salicylate, octyl salicylate and homomenthyl salicylate.

17. A method according to claim 16, wherein the weight ratios of tris(2-ethylhexyl)4,4',4"-(1,3,5-triazine-2,4,6-triyltriimino)-tris-benzoate and one or more salicylic acid derivatives are chosen from the range 1:10 to 10:1.

18. A method according to claim 17, wherein the weight ratios of tris (2-ethylhexyl) 4,4',4"-(1,3,5-triazine-2,4,6-triyltriimino)-tris-benzoate and one or more salicylic acid derivatives are chosen from the range 1:4 to 4:1.

19. A method according to claim 16, wherein the total amount of tris(2-ethylhexyl) 4,4',4"-(1,3,5-triazine-2,4,6-triyltriimino)-tris-benzoate in the formulation is chosen from the range 0.1–10.0% by weight based on the total weight of the formulation.

20. A method according to claim 19, wherein the total amount of tris(2-ethylhexyl) 4,4',4"-(1,3,5-triazine-2,4,6-triyltriimino)-tris-benzoate in the formulation is chosen from the range 0.5–6.0% by weight based on the total weight of the formulation.

21. A method according to claim 16, wherein the total amount of one or more substances chosen from the group consisting of monoesters and diesters of branched alkanecarboxylic acids having a chain length of 10–24 carbon atoms and diglycerol or triglycerol in the formulation is chosen from the range of 0.1–25.0% by weight based on the total weight of the formulation.

22. A method according to claim 21, wherein the total amount of one or more substances chosen from the group consisting of monoesters and diesters of branched alkanecarboxylic acids having a chain length of 10–24 carbon atoms and diglycerol or triglycerol in the formulation is chosen from the range of 0.5–15.0% by weight based on the total weight of the formulation.

* * * * *